United States Patent
Giebler

[11] Patent Number: 5,811,659
[45] Date of Patent: Sep. 22, 1998

[54] INFUSION HOSE FOR AN INFUSION DEVICE WITH A BUBBLE DETECTOR

[76] Inventor: Fritz Giebler, Waltershofener Str. 16, D-86405 Meitingen, Germany

[21] Appl. No.: 702,540

[22] PCT Filed: Dec. 29, 1995

[86] PCT No.: PCT/EP95/05168

§ 371 Date: Sep. 4, 1996

§ 102(e) Date: Sep. 4, 1996

[87] PCT Pub. No.: WO96/20746

PCT Pub. Date: Jul. 11, 1996

[30] Foreign Application Priority Data

Jan. 4, 1995 [DE] Germany ................ 195 00 154.0

[51] Int. Cl.$^6$ .................................................. G01N 29/00
[52] U.S. Cl. ................................ 73/19.03; 604/65
[58] Field of Search ................... 73/19.03, 861.04; 340/621, 632; 604/65, 122

[56] References Cited

U.S. PATENT DOCUMENTS

| | | | |
|---|---|---|---|
| 4,043,193 | 8/1977 | Bailey | 73/152.22 |
| 4,068,521 | 1/1978 | Cosentino | 73/19.03 |
| 4,114,144 | 9/1978 | Hyman | 340/632 |
| 4,137,940 | 2/1979 | Faisandier | 137/486 |
| 4,237,720 | 12/1980 | Abts | 73/19 |
| 4,312,341 | 1/1982 | Zissimopoulos | 604/67 |
| 4,418,565 | 12/1983 | St | 73/19.03 |
| 4,454,759 | 6/1984 | Pirkle | 73/299 |
| 4,465,063 | 8/1984 | Nielsen et al. | 128/1 D |
| 4,496,346 | 1/1985 | Mosteller | 604/123 |
| 4,638,662 | 1/1987 | Watson | 73/302 |
| 4,649,739 | 3/1987 | Horner | 73/49.2 |
| 4,651,555 | 3/1987 | Dam | 73/19.03 |
| 4,658,244 | 4/1987 | Meijer | 340/632 |
| 4,668,945 | 5/1987 | Aldrovandi | 340/621 |
| 4,949,572 | 8/1990 | Wilen | 73/53.01 |
| 5,026,348 | 6/1991 | Venegas | 604/122 |
| 5,064,412 | 11/1991 | Henke | 604/65 |
| 5,102,392 | 4/1992 | Sakai | 604/122 |
| 5,123,275 | 6/1992 | Daoud | 73/19.03 |
| 5,175,709 | 12/1992 | Slayton et al. | 367/90 |
| 5,177,993 | 1/1993 | Beckman | 73/19.03 |
| 5,205,153 | 4/1993 | Hlavinka et al. | 73/79.03 |
| 5,269,188 | 12/1993 | Esin | 73/610 |
| 5,349,852 | 9/1994 | Kamen | 73/149 |
| 5,535,633 | 7/1996 | Kofoed et al. | 73/861.052 |
| 5,600,073 | 2/1997 | Hil | 73/861.04 |

FOREIGN PATENT DOCUMENTS

| | | |
|---|---|---|
| 0 053 453 A1 | 6/1982 | European Pat. Off. . |
| 0 524 605 A1 | 1/1993 | European Pat. Off. . |
| 3121429 A1 | 2/1983 | Germany . |
| 3141576 A1 | 5/1983 | Germany . |

*Primary Examiner*—Hezron E. Williams
*Assistant Examiner*—Jay L. Politzer
*Attorney, Agent, or Firm*—Lappin & Kusmer LLP

[57] ABSTRACT

On an infusion hose for an infusion device on which a column of liquid is permanently maintained at least in one section of the infusion hose and on which adjacent to that section there is arranged ultrasound detector equipment the acoustic signal from which passes through the column of liquid and is used to detect inclusions of air in the column of liquid, the section of the infusion hose, with reference to the said infusion hose, incorporates substantially diametrically opposed contacts (3, 6) for making contact with the ultrasound transmitter and receiver, and the contacts (3, 6) are insulated from the surrounding region of the section by acoustic filters and/or dampers (2, 4).

2 Claims, 1 Drawing Sheet

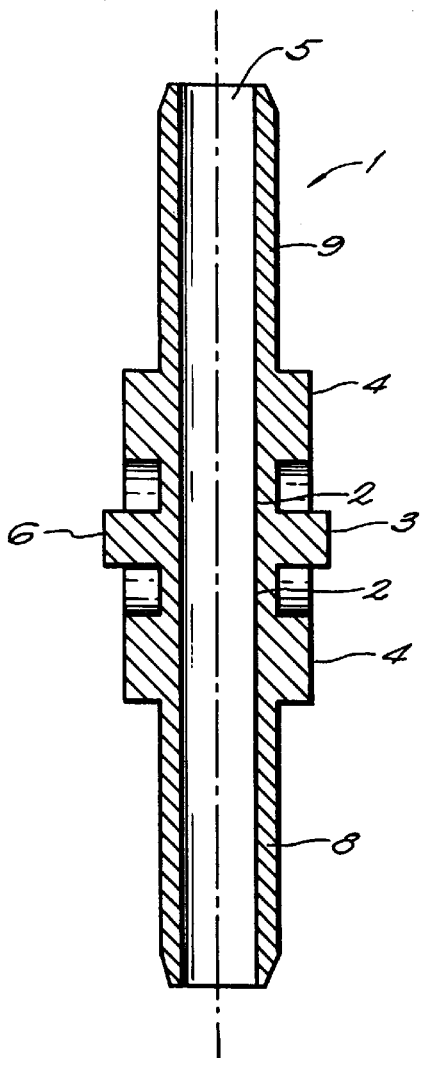
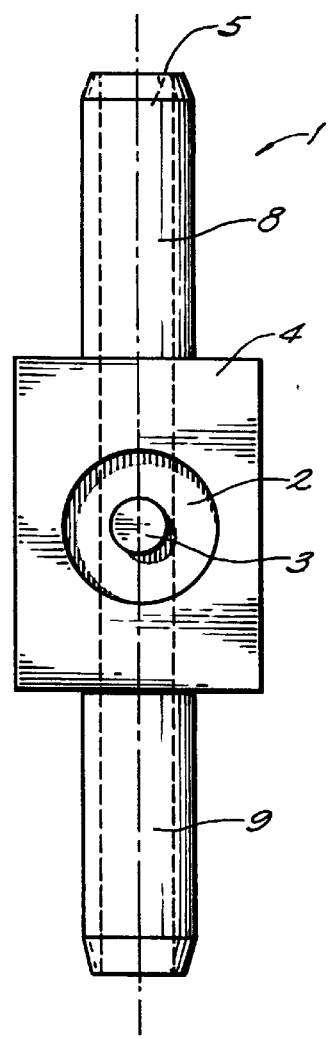
FIG. 1  FIG. 2
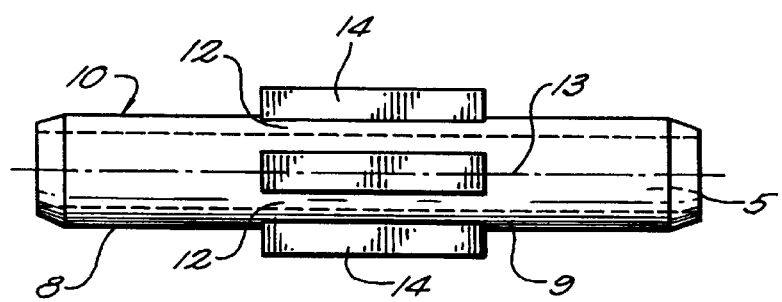
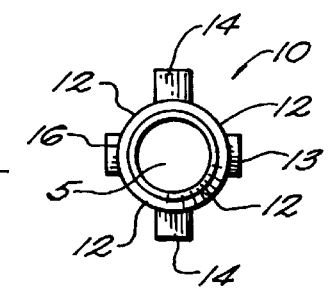
FIG. 3  FIG. 4

INFUSION HOSE FOR AN INFUSION DEVICE WITH A BUBBLE DETECTOR

The invention relates to an infusion hose for an infusion device with a bubble detector of the type specified in the preamble of claim 1.

When infusion devices are used in medical applications the column of liquid in the infusion hose is monitored for included bubbles of air, for such air bubbles must not be allowed to pass into the patient's bloodstream.

Although a wide variety of methods is available for monitoring the column of liquid for included air bubbles, the use of ultrasound sensors is preferred.

On such method and apparatus for carrying out this method are for example described in unexamined German Patent Application DE-OS 3141576. This involves arranging an ultrasound transmitter plate and an ultrasound receiver plate on the mutually facing inner surfaces of the free side-pieces of a U-shaped supporting body, the distance between the ultrasound transmitter plate and the ultrasound receiver plate being such that the hose or line is squeezed between these plates, deforming its circular cross-section. The size of the signal received by the ultrasound receiver will depend on whether there is liquid or air in the infusion hose in the region of the acoustic signal, thereby enabling the electrical signal output from the ultrasound receiver to be evaluated and used to detect air inclusions.

Undesirably, however, the transmitted acoustic signal is relayed not only by the column of liquid, or rather inclusions of air, but also by the free hose sections which form between the free side-pieces of the U-shaped supporting body, with the result that the signal-to-noise ratio is small and this may mean that perfectly reproducible results are not obtained.

This problem is further intensified by the fact that in many cases a plastics body fitting exactly into a mating part in the infusion device is drawn over the infusion hose to produce a good contact with the ultrasound transmitter and receivers and to fix the position of the hose. This plastics body may also be a specially shaped connection nipple featuring two connection fittings to which two different grades of hose are joined, particularly when an infusion device with a roller pump is used on which the hose segment located in the roller pump is silicone hose whilst a less expensive material is used for the remaining part of the infusion hose.

Although this plastics body makes it possible to properly position the ultrasound transmitter and receiver, it very strongly conducts the acoustic signal independently of the hose, thereby further deteriorating the signal-to-noise ratio.

It is the object of the invention to create an infusion hose for an infusion device with a bubble detector of the type mentioned at the beginning that makes it possible for air inclusions in the column of liquid to be detected better.

This object is achieved by the features indicated in claim 1.

Advantageous embodiments and refinements of the invention can be taken from the subsidiary claims.

Designing the infusion hose in accordance with the invention enables the acoustic signal to be communicated in a defined manner to the column of liquid, or rather to the interior of the infusion hose, thereby enabling reproducible results with a high signal-to-noise ratio to be obtained which can be satisfactorily reproduced, since the contacts and the filters and/or dampers can be manufactured both inexpensively and in an accurately reproducible manner by straightforward shaping of a plastics part.

The plastics body is preferably constructed as a connection nipple for connecting two hose sections of the infusion hose made from different materials, or alternatively it may be drawn onto an infusion hose in a tight fit.

Additional measuring elements may also be arranged inside the plastics body, for example an impeller wheel used to monitor the rate of flow; the path travelled by this movable body intersects the acoustic signal and thus the movement of this movable body can be derived in the electric signal output by the ultrasound receiver.

The invention will now be explained in more detail with reference to examples of embodiment represented in the drawing, wherein:

FIG. 1 shows a sectional view of a first form of embodiment of a section of the infusion hose;

FIG. 2 shows a side view of the section of infusion hose seen in FIG. 1;

FIG. 3 shows a second form of embodiment of a section of the infusion hose;

FIG. 4 is a cross-sectional view of the section seen in FIG. 3.

The first embodiment of the hose section depicted in FIGS. 1 and 2 is constructed in the form of an elongate plastics body 1 which at both its axial extremities features respective hose fittings 8, 9 which are used to push on respective further segments of the infusion hose, which may be made from different materials. The plastics body 1 incorporates a continuous flow duct 5 into which a continuous infusion hose may naturally also be inserted with a tight fit.

In the central region of the plastics body 1 there is provided a reinforced plastics block 4 in which, on diametrically opposing faces of the flow duct 5, are formed contacts 3, 6 which are connected to the remaining part of the plastics block 4 via an annulus-shaped area 2 of small cross-section and hence lesser mass. These areas 2 of reduced cross-section and hence reduced mass constitute an acoustic filtering element and insulate the contacts 3, 6 from the rest of the plastics block 4, with the result that an acoustic signal for example fed into the contact 3 is only propagated outwards to a small extent in the radial direction of the attenuated areas 2 and the remaining part of the acoustic signal is definitively attenuated and absorbed in the surrounding area 4 of the plastics block. This enables reproducible ratios to be obtained, and the ultrasound transmitters and receivers coupled to the free ends of the contacts 3, 6 are satisfactorily coupled to the column of liquid in the flow duct 5.

FIGS. 3 and depict a further embodiment of the section of the infusion hose; this embodiment likewise features a plastics body 10 which is provided with two connection fittings 8, 9 for joining to respective segments of the infusion hose.

This plastics body 10 likewise features a flow duct 5 running axially through it. Around this flow duct, in the central region of the plastics body 1, are alternately positioned elongate projections 13, 16 of lesser mass and projections 14 of greater mass, which are separated from one another in the circumferential direction by areas 12 of lesser mass. These areas 12 produce an insulating and filtering effect, whereas the projections 14 product damping, with the result that acoustic signals injected into or out of the projections 13, 16 are very highly insulated from the rest of the plastics body 10 and the projections 14 having the greater mass dampen any remaining acoustic oscillations.

It is of course possible to arrange movable bodies, shown at 17 in FIG. 1, for example floats, inside the plastics body, 1 or 10, the said floats being deflected by the flow of liquid, or else an impeller wheel driven by the flow of liquid; the path travelled by these moving bodies intersects the path of the acoustic signal and the said acoustic signal can thus simultaneously by used to measure the flow.

I claim:

1. An infusion hose for an infusion device having a bubble detector, in which a column of liquid is maintained permanently at least in one section of the infusion hose and in which adjacent to this section is arranged ultrasound detector equipment incorporating an ultrasound transmitter and receiver positioned so that an acoustic signal from the transmitter passes diametrically through the column of liquid in the section of infusion hose to the receiver, the acoustic signal being used to detect inclusions of air in the column of liquid, characterized in that the section of infusion hose includes (a) substantially diametrically opposed contacts (3, 6; 13, 16) for making acoustic contact with the ultrasound transmitter and receiver, respectively, and (b) acoustic dampers (2, 4; 12, 14) for insulating the contacts (3, 6; 13, 16) from the surrounding area of the section, wherein the dampers (2, 4; 12, 14) each include an area (2; 12) of lesser mass surrounding the respective contact (3, 6; 13, 16) and an area (4; 14) of increased mass surrounding the area of lesser mass.

2. The infusion hose according to claim 1, characterized in that said section is constituted by a plastics body (1) in which are integrally formed the contacts (3, 6; 13, 16) and the acoustic dampers (2, 4; 12, 14).

\* \* \* \* \*